US008561282B2

(12) United States Patent
Hirota

(10) Patent No.: US 8,561,282 B2
(45) Date of Patent: Oct. 22, 2013

(54) METHOD OF COUPLING CONTAINER BODY AND COVER MEMBER

(75) Inventor: Sachiyo Hirota, Tokyo (JP)

(73) Assignee: Nosaka Tec Co., Ltd., Fukui (JP)

( * ) Notice: Subject to any disclaimer, the term of this patent is extended or adjusted under 35 U.S.C. 154(b) by 185 days.

(21) Appl. No.: 13/143,946

(22) PCT Filed: Jan. 19, 2010

(86) PCT No.: PCT/JP2010/050530
§ 371 (c)(1),
(2), (4) Date: Jul. 11, 2011

(87) PCT Pub. No.: WO2010/090067
PCT Pub. Date: Aug. 12, 2010

(65) Prior Publication Data

US 2011/0277300 A1 Nov. 17, 2011

(30) Foreign Application Priority Data

Feb. 4, 2009 (JP) ................................ 2009-023625

(51) Int. Cl.

| | |
|---|---|
| ***B23Q 3/00*** | (2006.01) |
| ***B65B 67/02*** | (2006.01) |
| ***B65B 1/00*** | (2006.01) |
| ***B65B 3/00*** | (2006.01) |
| ***B65B 5/00*** | (2006.01) |
| ***B65B 7/28*** | (2006.01) |
| ***B65B 31/00*** | (2006.01) |
| ***B65B 55/00*** | (2006.01) |
| ***B67B 3/28*** | (2006.01) |
| ***B23P 21/00*** | (2006.01) |
| ***B23P 17/00*** | (2006.01) |
| ***A61K 9/48*** | (2006.01) |

(52) U.S. Cl.
USPC .................. 29/464; 53/432; 53/281; 53/471; 53/510; 53/900; 29/469; 29/530; 424/451

(58) Field of Classification Search
USPC ........... 29/428, 463, 464, 469, 530; 221/135; 424/451; 53/281, 432, 471, 510, 900
See application file for complete search history.

(56) References Cited

U.S. PATENT DOCUMENTS

| | | | | |
|---|---|---|---|---|
| 3,552,095 A * | 1/1971 | Inman et al. | .................... | 53/390 |
| 3,800,399 A * | 4/1974 | Warrick et al. | ............. | 29/403.3 |

(Continued)

FOREIGN PATENT DOCUMENTS

| | | |
|---|---|---|
| JP | 6-092393 | 4/1994 |
| JP | 11-059602 | 3/1999 |

(Continued)

OTHER PUBLICATIONS

International Search Report issued Mar. 23, 2010 in International (PCT) Application No. PCT/JP2010/050530.

*Primary Examiner* — Essama Omgba
*Assistant Examiner* — Darrell C Ford
(74) *Attorney, Agent, or Firm* — Wenderoth, Lind & Ponack, L.L.P.

(57) ABSTRACT

A method of coupling a container body (2) and a cover member (3) in a capsular container (1) includes a filling step for filling liquid medicine, powdered medicine, or granular medicine in the container body (2), and a fitting step for fitting the container body (2) to the cover member (3) under an atmosphere at a negative pressure which is lower than atmospheric pressure. Consequently, the pressure inside the joined container (1) does not exceed atmospheric pressure, the filling (37) which fills the inside of the container (1) can be prevented from leaking out between the container body (2) and the cover (3), and it is also possible to prevent bending of the container (1) which starts from the weak portion of the container (1).

1 Claim, 7 Drawing Sheets

(56) References Cited

U.S. PATENT DOCUMENTS

| | | | | | |
|---|---|---|---|---|---|
| 3,893,278 | A | * | 7/1975 | Lewis | 53/401 |
| 3,927,195 | A | * | 12/1975 | Messora | 424/454 |
| 3,972,155 | A | * | 8/1976 | Mahaffy et al. | 53/453 |
| 4,089,152 | A | * | 5/1978 | Zanasi | 53/281 |
| 4,581,875 | A | * | 4/1986 | MacLaughlin et al. | 53/467 |
| 4,615,165 | A | * | 10/1986 | Gamberini | 53/282 |
| 4,667,455 | A | * | 5/1987 | Morrow | 53/471 |
| 4,820,364 | A | * | 4/1989 | Graham | 156/69 |
| 4,828,142 | A | * | 5/1989 | McKnight | 221/171 |
| 4,964,262 | A | * | 10/1990 | Moser et al. | 53/506 |
| 5,081,822 | A | * | 1/1992 | Boyd et al. | 53/468 |
| 5,094,184 | A | * | 3/1992 | Yamamoto et al. | 118/233 |
| 5,101,612 | A | * | 4/1992 | Yamamoto et al. | 53/499 |
| 5,191,741 | A | * | 3/1993 | Jones | 53/475 |
| 5,397,018 | A | * | 3/1995 | Mader | 221/102 |
| 5,632,971 | A | * | 5/1997 | Yang | 428/34.1 |
| 5,690,958 | A | * | 11/1997 | McGrath | 424/451 |
| 6,170,226 | B1 | * | 1/2001 | Chang | 53/64 |
| 6,499,279 | B1 | * | 12/2002 | Yamamoto et al. | 53/560 |
| 6,546,702 | B1 | * | 4/2003 | Pickett | 53/485 |
| 6,770,118 | B2 | * | 8/2004 | Stolyarevsky | 95/90 |
| 6,901,972 | B1 | * | 6/2005 | Nelson | 141/67 |
| 7,082,738 | B2 | * | 8/2006 | Konishi et al. | 53/281 |
| 7,469,519 | B2 | * | 12/2008 | Barthel et al. | 53/433 |
| 7,905,258 | B2 | * | 3/2011 | Bedeschi | 141/51 |
| 8,467,899 | B2 | * | 6/2013 | Karwacki et al. | 700/244 |
| 2007/0068959 | A1 | * | 3/2007 | D'Silva | 221/7 |
| 2007/0193225 | A1 | * | 8/2007 | Bailey et al. | 53/281 |
| 2008/0011386 | A1 | * | 1/2008 | Bedeschi | 141/59 |
| 2009/0166370 | A1 | | 7/2009 | De Turk et al. | |
| 2010/0063486 | A1 | * | 3/2010 | Dijksman et al. | 604/890.1 |
| 2011/0062036 | A1 | * | 3/2011 | Xie et al. | 206/222 |
| 2013/0081358 | A1 | * | 4/2013 | Boldis et al. | 53/408 |

FOREIGN PATENT DOCUMENTS

| | | | |
|---|---|---|---|
| JP | 2005-531334 | | 10/2005 |
| JP | 2007-144014 | | 6/2007 |
| WO | WO 03034444 A1 | * | 4/2003 |

* cited by examiner

METHOD OF COUPLING CONTAINER BODY AND COVER MEMBER

BACKGROUND OF THE INVENTION

1. Technical Field

The present invention relates to a method of filling liquid, powdered substances or granular substances into a capsule-type container configured by fitting a container body and a cover member to each other and then coupling the cover member to the container body.

2. Background Art

FIG. 1 shows a general container form known in the prior art, and the container includes a container body having a cylindrical portion and a closed bottom portion and a cover member having a cylindrical portion and a closed top portion, and the outer diameter of the container body is smaller than the outer diameter of the cover member. It is also possible to define the member having a larger diameter to be a container body as a matter of course, but the member having a smaller diameter is defined as the container body in this drawing. Incidentally, this container is filled with liquid medicine, powdered medicine, or granular medicine or the like.

In case of filling the above-described container with medicine, the cover member is removed and separated from the container body, the container body in a state in which an upper end is open is filled with medicine, then the cover member is fitted thereto, and then the cover member is sealed by gluing or the like so as not to be detached, and is dried. Vacant containers in a state in which the cover members are provisionally coupled by being fitted to the container bodies are stored in a hopper of an apparatus shown in FIG. 7 at random, the containers are taken out from the hopper by a predetermined number of those, the cover members are removed, the container bodies are filled with medicines, the cover members are coupled by being fitted again, and then the cover members are sealed so as not to be detached.

JP-A-11-59602 discloses an apparatus for filling containers with a medical product, including an alignment apparatus configured to align containers in the vertical direction so that upper shells of the containers come to upper sides, and the containers aligned in this manner are supplied to a removing apparatus configured to remove the upper shells, and including at least one apparatus configured to verify non-existence of the container and transport means configured to transport the containers in a still closed state from the alignment apparatus to the removing apparatus via a verification apparatus.

The "apparatus configured to measure and fill medicine to a storage container, specifically to a container" according to JP-A-6-92393 is an apparatus including an apparatus operated continuously and being simple and having reliability for verifying existence of the containers, and is configured to measure and fill the medicine which is designed to be applied easily to both liquid and paste filled substances.

In other words, it is made up of a rotating bottom portion formed with holes to be engaged with movable pistons, a belt for transporting containers, a rotating top portion having a container for medicine, a rotating center portion integral with the bottom portion and the top portion, a hole formed at the center portion, one valve configured to travel between a first position where respective pistons move downward and are drawn into medicine and a second position where the pistons are moved upward, openings are open, and a predetermined amount of medicine is supplied to the containers located below; and a mechanism configured to control the movement of another valve.

In this manner, there exist various types of apparatuses for filling containers with medicines or other substances. Basically, the cover member is removed, and the container body is filled with medicine or the like, and then, the cover member is put on and coupled with the container body. Although there is no significant problem when the filled substance is powdered substances or granular substances, when filling the container body with liquid, fitting tolerance between the container body and the cover member is strictly set to be fine, so that leakage of the liquid is avoided by placing and coupling the cover member. Therefore, in such a case, when putting the cover member on the container body and coupling the same, the internal pressure in the container after having been coupled is increased.

In other words, since the fitting tolerance between the container body and the cover member is small and strict, air in the interior thereof cannot flow out when coupling the cover member, and hence the state of the internal pressure becomes high after the coupling. Therefore, the air in the interior of the container tries to flow out to make the internal pressure in the container equal to the atmospheric pressure. However, there arises a phenomenon such that liquid or the like filled therein leaks from the fitting clearance between the container body and the cover member in association with the flow of the air.

Also, in a case where the internal pressure of the container is increased due to the coupling between the container body and the cover member, when performing band sealing subsequently, a portion where the band sealing liquid is applied is instantaneously melted and softened and is bent at a weak portion on the circumference of the container as an anchor point due to the internal pressure of the container. In other words, when the internal pressure of the container is increased, a phenomenon such that the container by itself is bent into a banana shape occurs. In contrast, in the prior art, there is a case where the speed of coupling between the container body and the cover member is reduced in order to restrain the pressure in the interior of the container from rising at the time of coupling between the container body and the cover member. However, there is a problem of lowering of productivity because of the reduction of the speed of coupling.

SUMMARY OF THE INVENTION

The problems to be solved by the present invention are problems described above, and it is an object of the present invention to provide a method of coupling without increasing the pressure in the interior of the container when putting a cover member on a container body and coupling the same, while maintaining high productivity.

A container according to the present invention is made up of a container body having a first cylindrical portion and a closed bottom portion and a cover member having a second cylindrical portion and a closed top portion, and the container body and the cover member are coupled by fitting the first cylindrical portion of the container body and the second cylindrical portion of the cover member so as to be overlapped with respect to each other, thereby forming the container. A method of coupling the container body and the cover member according to the present invention includes a filling step of filing liquid medicine, powdered medicine, or granular medicine into the container body and, subsequently a fitting step of fitting the container body to the cover member having the second cylindrical portion and the closed top portion to form a filled container under an atmosphere having a negative pressure lower than the atmospheric pressure. In other words, the method of coupling the container body and the cover member in the present invention is configured to achieve fitting so as not increase the internal pressure upon the fitting described above, thereby achieving a pressure in the interior of the container to be substantially the same as the atmospheric air or not exceeding the atmospheric pressure in the coupled state.

Also, the fitting step of the method of coupling the container body and the cover member according to the present invention is performed for example by using a jig including a container body receiver arranged on the lower side and a cover member receiver arranged on the upper side. In the example of the preferred jig, the container body receiver includes a first inner wall defining a receiving portion for fitting the container body, an inner wall bottom formed at a bottom portion of the first inner wall for placing the closed bottom portion of the container body, and a through hole formed on the inner wall bottom so as to be arranged coaxially with the receiving portion, the cover member receiver includes a second inner wall defining a hole portion having substantially the same diameter as the receiving portion and a shoulder portion formed on an upper portion of the cover member receiver for placing so as to fit an open lower end portion of the above-described cover member. The above-described shoulder portion is formed into an annular shape arranged coaxially with the second inner wall. The container body receiver and the cover member receiver are disposed so that the receiving portion and the hole portion are coaxial with each other and form the jig. In addition, the second inner wall and the first inner wall including the inner wall bottom and a side wall of the through hole are formed with first grooves, second grooves and third grooves communicating with each other. A pipe is disposed on the lower side of the container body receiver so as to communicate with the above-described third groove, and a push-up pin movable in the vertical direction is disposed in the pipe so as to be arranged coaxially with the through hole. Preferably, according to the method of coupling the container body and the cover member of the present invention, in the fitting step, the container body is fitted to the receiving portion, the cover member is placed on the cover member receiver so that the open lower end portion is fitted to the shoulder portion, the cover member receiver is placed on top of the container body receiver so that part of the container body is inserted into the hole portion, the push-up pin is driven upward via the through hole to bring the same into abutment with the closed bottom portion of the container body and, in addition, to push the container body up with the push-up pin and fit the same with the cover member in a state in which gas in the receiving portion and the hole portion is sucked via the pipe and grooves, whereby the container body is fitted to the cover member under an atmosphere having a negative pressure lower than the atmospheric pressure.

Here, since there exist various detailed means for generating negative pressures, the present invention is not specifically limited and, for example, it is also possible to bring the entire apparatus or a part of it in which the coupling step is performed into a sealed state and performing sucking with an air pump or a blower. It is also possible to create a state under a negative atmosphere lower than the atmospheric pressure by sucking only a limited portion in which the cover member is coupled to the container body in the fitting step.

According to the method of coupling the container of the present invention, since the step of covering the cover member to the container body and fitting the same thereto is performed under the negative atmosphere, the inner capacity is reduced by coupling the cover member so that the pressure is substantially the same as the atmospheric pressure. In other words, since the internal pressure does not exceed the atmospheric pressure in the state in which the cover member is coupled, after having coupled the container body and the cover member, air does not flow out due to the internal pressure in the container in the coupled state, liquid or the like filled in the interior of the container can be prevented from leaking from a gap between the container body and the cover member.

In addition, in a case where the coupled joint is band-sealed after having coupled the container body and the cover member, even when a portion where band sealing liquid is applied is instantaneously melted and softened, since the internal pressure in the container is the same as the atmospheric pressure, bending at a weak portion on the circumference of the container as an anchor point due to the internal pressure of the container is prevented. In other words, a phenomenon such that the container by itself is bent into a banana shape does not occur as described above.

In addition, in the prior art, there is a case where the speed of coupling between the container body and the cover member is reduced in order to restrain the pressure in the interior of the container from rising at the time of coupling between the container body and the cover member and, in such a case, the productivity is lowered. However, according to the present invention, the pressure in the interior of the container does not increase even when the container body and the cover member are coupled quickly, so that decrease of productivity is not caused thereby.

DETAILED DESCRIPTION OF THE INVENTION

Figure 1:
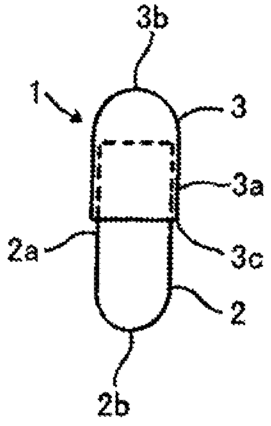
FIG. 1 PRIOR ART
FIG. 1 is a front view showing a detailed example of a container as an object of a method of coupling in the present invention.

FIG. 1 is a front view showing a detailed example of a container as an object of a method of coupling according to the present invention, in which a container 1 includes a container body 2 and a cover member 3, the container body 2 includes a first cylindrical portion 2*a* and a closed bottom portion 2*b*, and the cover member 3 includes a second cylindrical portion 3*a* and a closed top portion 3*b* and an open lower end portion 3*c*. The outer diameter of the first cylindrical portion 2*a* is smaller than the outer diameter of the second cylindrical portion 3*a*. In other words, the container body 2 is formed to be thinner than the cover member 3.

The present invention is a method of coupling the container body 2 and the cover member 3 by fitting the cover member 3 to the container body 2 alter filling the container body 2 with liquid medicine, powdered medicine, or granular medicine, which is configured so that the pressure in the interior of the container does not rise in this fitting step. Incidentally, when filling with the above-described liquid-state medicine, the powered medicine, or the granular medicine, the cover member 3 fitted to the body in advance is removed and the container body 2 is filled therewith, then the cover member 3 is coupled and glued (sealed) so as not to be detached, and then dried.

Figure 2A:
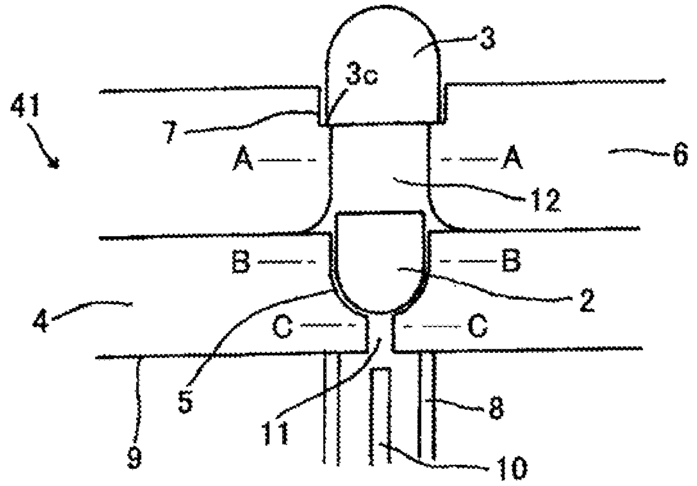
FIGS. 2A to 2C are diagrammatic drawings showing procedures of a fitting step in which a cover member is attached to a container body according to an embodiment of the present invention.
Figure 2B:
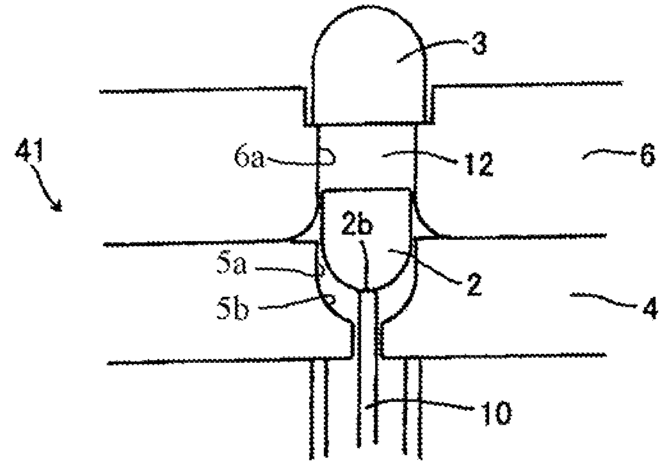
Figure 2C:
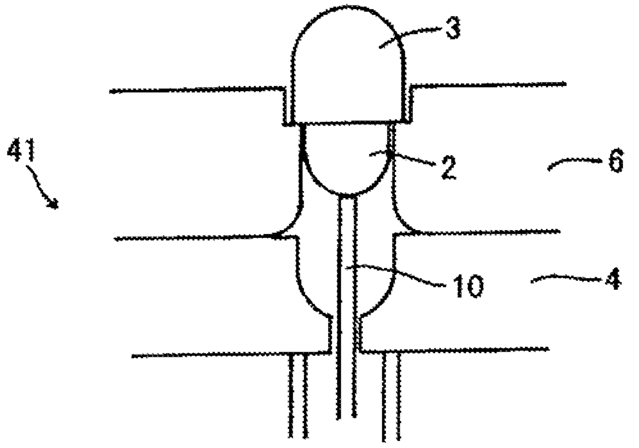

FIGS. 2A, 2B and 2C show a procedure of the fitting step in an embodiment of the present invention, and the fitting step is performed using a jig 41 made up of a container body receiver 4 arranged on the lower side and a cover member receiver 6 arranged on the upper side. The container body receiver 4 includes a first inner wall 5*a* configured to define a receiving portion 5 for fitting the container body, an inner wall bottom 5*b* configured to place the closed bottom portion 2*b* of the container body 2, and a through hole 11 formed on the inner wall bottom 5*b* so as to be arranged coaxially with the receiving portion 5. Also, the cover member receiver 6 includes a second inner wall 6*a* configured to define a hole portion 12 having substantially the same diameter with the receiving portion 5, and a shoulder portion 7 formed on an upper part of the cover member receiver 6 for placing the open lower end portion 3*c* of the cover member 3 so as to be fitted thereto. For reference sake, the shoulder portion 7 is formed in an annular shape so as to be arranged coaxially with the second inner wall 6*a*. Therefore, the hole portion 12 formed so as to penetrate through the cover member receiver 6 has an inner diameter smaller than the shoulder portion 7, and is formed so as to be arranged coaxially with the shoulder portion 7. The container body receiver 4 and the cover member receiver 6 are disposed so that the receiving portion 5 and the hole portion 12 are arranged coaxially with each other and form the jig 41.

In the procedure of FIG. 2A, the container body 2 and the cover member 3 are separated, and the container body 2 is fitted to the receiving portion 5 provided on the container body receiver 4 in a state in which the container body 2 is almost fully filled with a liquid medicine 37. Then, the cover member 3 is also fitted to the shoulder portion 7 formed to the cover member receiver 6. Here, the container body receiver 4 and the cover member receiver 6 are disposed so that the above-described receiving portion 5 and the annular shoulder portion 7 are coaxial with each other. In addition, the second inner wall 6*a* and the first inner wall 5*a* including the inner wall bottom 5*b* and the side wall of the through hole 11 are formed with first grooves 13, second grooves 14, and third grooves 15, communicating with each other.

A pipe 8 is disposed under the container body receiver 4, an upper end of the pipe 8 comes into contact with a lower surface 9 of the container body receiver 4, and the pipe 8 communicates with the above-described third grooves 15. Aso, a push-up pin 10 is disposed at the center of the pipe 8. The push-up pin 10 is disposed so as to be arranged coaxially with the through hole 11 formed on the inner wall bottom 5*b* of the container body receiver 4.

Figure 3:
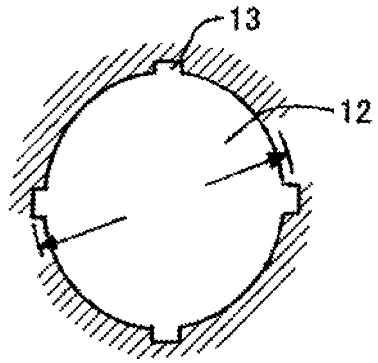
FIG. 3 is an enlarged cross-sectional view of the container shown in the procedure of FIG. 2A taken along the line A-A.

FIG. 3 is an enlarged cross-sectional view taken along the line A-A in FIG. 2A. As shown in this drawing, the first grooves 13 extending in the vertical direction are formed around the hole portion 12 at four positions, and penetrate downward from the bottom of the receiving portion 5. Here, since the distance between the opposed first grooves 13 is smaller than the outer diameter of the cover member 3, upper ends of the first grooves 13 are closed by the open lower end portion 3*c* of the cover member 3 fitted to the shoulder portion 7.

Figure 4:
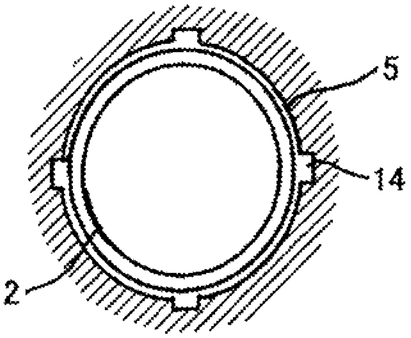
FIG. 4 is an enlarged cross-sectional view of the container shown in the procedure of FIG. 2A taken along the line B-B.
Figure 5:
FIG. 5 is an enlarged cross-sectional view of the container shown in the procedure of FIG. 2A taken along the line C-C.

FIG. 4 shows an enlarged cross-sectional view taken along the line B-B in FIG. 2A. In other words, it is an enlarged cross-sectional view of the receiving portion 5. The container body 2 is fitted in the receiving portion 5, and the second grooves 14 are formed around the receiving portion 5 at four positions, and are formed along an inner surface of the receiving portion 5. Also, FIG. 5 shows an enlarged cross-sectional view taken along the line C-C shown at a portion of the through hole 11 in FIG. 2A. The third grooves 15 are formed also around the through hole 11 at four positions, and the third grooves 15 communicate with the second grooves 14 formed on the above-described receiving portion 5.

In other words, the second grooves 14 and the third grooves 15 communicate with each other from an upper end surface to a lower end surface of the container body receiver 4.

FIG. 2B shows a state in which the push-up pin 10 moved upward abuts with the closed bottom portion 2*b* of the container body 2, and the container body 2 is in the course of rising. The container body 2 fitted to the receiving portion 5 is separated from the inner wall bottom 5*b* and is moved upward, and is partly fitted to the hole portion 12 provided in the cover member receiver 6 and, at this time, an air pump (not shown) is used to perform suction via the above-described pipe 8, the third grooves 15, the second grooves 14, and the first grooves 13, whereby the pressure in the hole portion 12 is brought into a negative pressure lower than the atmospheric air.

In other words, when the suction is preformed via the pipe 8, the air is sucked via the third grooves 15 formed in the through hole 11, the second grooves 14 formed along the inner peripheral surface of the receiving portion 5, and the first grooves 13 provided around the hole portion 12, whereby the internal pressure of the hole portion 12 is lowered. Even when the container body 2 is fitted to the receiving portion 5 as shown in the FIG. 2A, or even when the container body 2 is moved upward by the push-up pin 10 as shown in the procedure (b), the suction is performed via the third grooves 15, the second grooves 14, the first grooves 13, provided respectively around the through hole 11, the receiving portion 5, and the hole portion 12 and the hole portion 12 is brought into a negative pressure.

Figure 6:
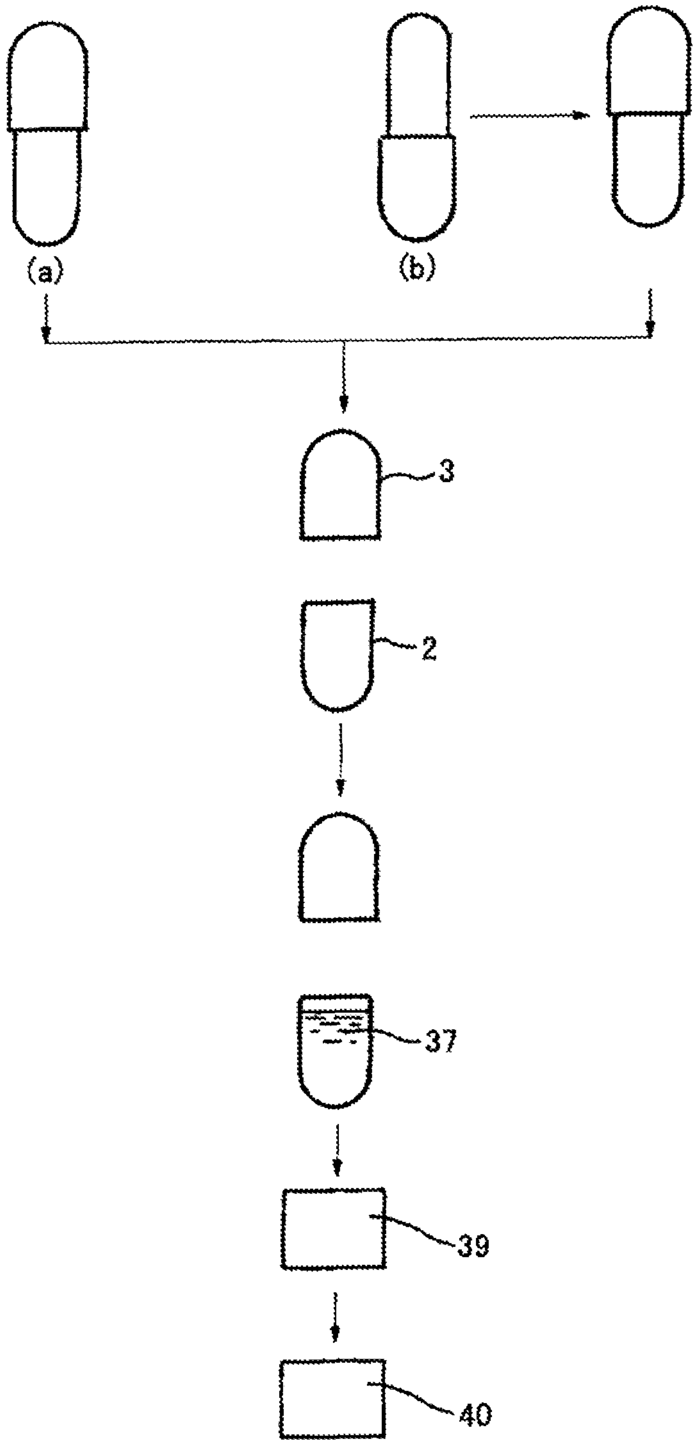
FIG. 6 is a diagrammatic drawing showing a general flow of a series of steps including a step of filling a container relating to the present invention with a substance.
Figure 7:
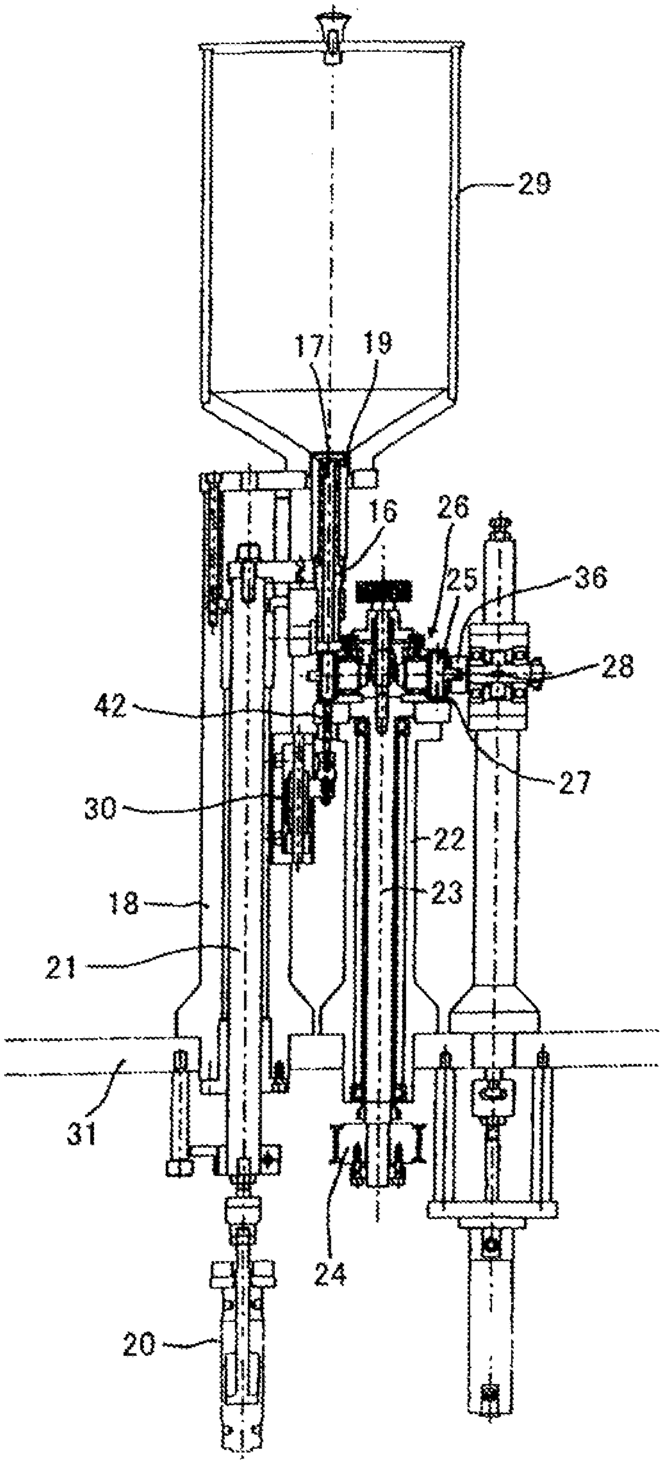
FIG. 7 is a diagrammatic drawing showing an embodiment of an inverting mechanism according to the present invention partly in cross section.

Incidentally, the containers 1 are randomly received in a hopper in the apparatus shown in FIG. 7 in a state in which the container bodies 2 and the cover members 3 are coupled, and each of the cover members 3 of the container 1, taken out one by one from the hopper, is removed and the liquid medicine 37 is filled therein. Then, the cover member 3 is covered and coupled as shown in FIGS. 2A to 2C, and then a sealing step 39 for sealing the coupled portion of the cover member 3 as shown in FIG. 6 and then a drying step 40 for drying the seal portion is performed.

In this case, the orientations of the containers 1 received in the hopper are random, and hence the orientations in which the containers are taken out are not constant, so that if the container body 2 is inversely oriented, the container body 2 cannot be filled with the liquid medicine 37. Accordingly, the orientation of the container 1 taken out from the hopper is corrected, and the cover member 3 is removed in a state in which the container body 2 is positioned on the lower side, and the container body 2 is filled with the liquid medicine 37 from an upper end opening.

The present invention relates to a method of coupling the container body 2 and the cover member 3, and is not intended to limit the method of taking out the containers 1 stored randomly in the hopper, and the inverting mechanism. However, for example, the containers 1 in the hopper drop into the receiving holes on a rotary body provided on an outer periphery of a turntable, and the container 1 dropped and received may be inversely oriented. In this case, the orientation is inverted and is aligned in the correct orientation. The containers 1 dropped and received in the correct orientation with the container body 2 on the lower side are kept as-is, and only the containers 1 dropped in an inverted orientation with the cover member 3 on the lower side are realigned, so that the orientations of all the containers 1 are unified.

When the container bodies 2 are unified with the container body 2 positioned on the lower side, the cover members 3 are removed, and the container bodies 2 are filled with the liquid medicine 37, or the powdered medicine or the granular medicine. Then, the cover members 3 are attached again and are sealed, and then dried. FIG. 6 shows a series of respective steps in which the container 1 drops from the hopper, the container body 2 is filled with the liquid medicine, or the powdered medicine or the granular medicine, and then is closed with the cover member 3 and dried. FIG. 2A shows the container 1 in the correct orientation with the container body 2 on the lower side, and FIG. 2B shows the container 1 in the inverted orientation with the cover member 3 on the lower side. Therefore, when the orientation of the container 1 dropped from the hopper is the inverted orientation as shown in FIG. 2B, the container 1 is inverted and then the cover member 3 is removed, and then the container body 2 is filled with the liquid medicine, or the powdered medicine or the granular medicine.

FIG. 7 is a diagrammatic drawing showing a detailed example of the inverting mechanism of the container 1, and reference numeral 29 in the same drawing designates a hopper, reference numeral 26 designates a turntable, and reference numeral 27 designates a rotary body. A number of containers 1 are randomly received in the hopper 29, and the containers 1 drop from a pit fall 17 of a pipe 16 extending downward of the center axis of the hopper 29.

The hopper 29 is attached to an upper end of a column 18 extending upright from a base 31 and a guiding pipe 19 is provided on an outer periphery of the above-described pipe 16 (the pipe 16 is fitted into the hole of the guiding pipe 19), and the guiding pipe 19 is attached so as to be movable in the vertical direction. In other words, the pipe 16 is fitted into the guiding pipe 19, and the upper end thereof is positioned on a center bottom of the hopper 29 so as to act on the containers 1 in the random state to be guided to the pit fall 17 of the pipe 16. Then, by the action of an air cylinder 20 provided on the base side, the guiding pipe 19 can be moved in the vertical direction via a rod 21. In other words, the guiding pipe 19 can be moved in the vertical direction synchronously with the intermitted rotary motion of the turntable 26 so as to allow the containers 1 in the hopper 29 to drop into the pit fall 17 one by one.

On the other hand, the turntable 26 is supported by a column 22 extending upright from the base 31, a supporting shaft 23 penetrates through the column 22, and the turntable 26 is attached to an upper end of the supporting shaft 23. A lower end portion of the supporting shaft 23 extends downward from the column 22, and a pulley 24 is attached to a lower end. Therefore, when the pulley 24 is rotated via a timing belt (not shown), the above-described turntable 26 can also be rotated. In this case, the turntable 26 is driven to rotate intermittently by 90°.

There are various mechanisms for driving the turntable 26 to rotate intermittently. In general, however, a cam is used, and the other pulley coupled to the pulley 24 via the timing belt is configured to perform intermittent motion by being attached to the cam. As the intermittent motion is generally used in a feeding apparatus or the like for feeding material to a press machine, description here will be omitted.

Then, although rotary bodies 27 having a horizontal axis in the radial direction are attached to an outer periphery of the turntable 26, the rotary body 27 includes a receiving hole 25 in which the container 1 is fitted in the vertical direction, and an engaging strip 28 is provided on the outside so as to project from the outer periphery of the turntable 26. Then, the container 1 dropped from the hopper 29 via the pit fall 17 is fitted into the receiving hole 25 of the rotary body 27. Then, a push-up pin 42 is provided downward of the receiving hole 25 of the rotary body 27, and the push-up pin 42 is allowed to be moved in the vertical direction by an air cylinder 30.

There are various height (length) dimensions of the container 1, a plurality of containers 1 are in a stack continuously in the pit fall 17, and hence a lower end portion of the container 1 positioned above may engage the receiving hole 25, and the container 1 is moved upward by the push-up pin 42. Therefore, the receiving hole 25 of the rotary body 27 can strictly be kept in a state in which only one piece of the container 1 is received, and the container 1 positioned above can be prevented from dropping and entering the receiving hole 25 by being sucked with air even when the push-up pin 42 is moved downward.

Figure 8A:
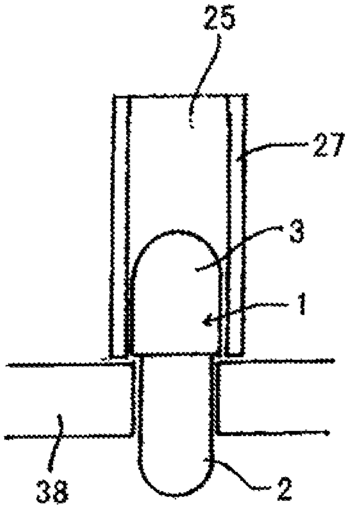
FIG. 8A is an enlarged diagrammatic drawing showing a state in which the container is received in a receiving hole in a rotary body in a state of correct orientation in which the container body is positioned on the lower side and the cover member is positioned on the upper side according to an embodiment of the present invention.
Figure 8B:
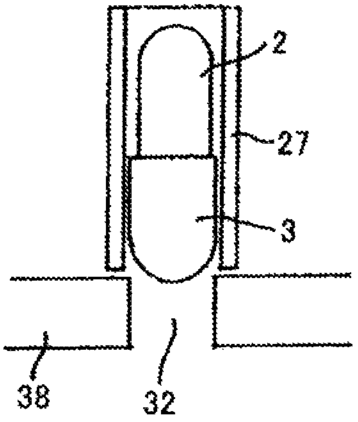
FIG. 8B is an enlarged diagrammatic drawing showing a state in which the container is received in the receiving hole in the rotary body in inversely oriented in which the container body is positioned on the upper side and the cover member is positioned on the lower side according to an embodiment of the present invention.

In this manner, the container 1 fitted into the receiving hole 25 of the rotary body 27 is moved to rotate by 90° in association with the rotation of the turntable 26 and, at this position, the orientation of the container 1 is verified. FIG. 8A and FIG. 8B are enlarged diagrammatic drawings showing states of the container 1 received in the receiving hole 25 of the rotary body 27, respectively. In FIG. 8A, the container 1 is in the correct orientation, and hence the container body 2 is positioned on the lower side and the cover member 3 is positioned on the upper side. In contrast, in FIG. 8B, the container 1 is in the inversely oriented state in which the container body 2 is positioned on the upper side and the cover member 3 is positioned on the lower side.

A substantially ring-shaped base 38 is provided on the lower side of the rotary body 27, and the container body 2 is fitted into a hole 32 formed on the base 38 and projects downward. However, in the case of being inversely oriented as shown in FIG. 8B, the outer diameter of the cover member 3 is too large to be fitted into the hole 32. Therefore, the container body 2 projecting downward of the base 31 may be detected by a sensor and the orientation of the container 1 can be known. In this manner, the receiving hole 25 of the rotary body 27 and the hole 32 of the base 38 are both a shouldered hole.

Figure 9:
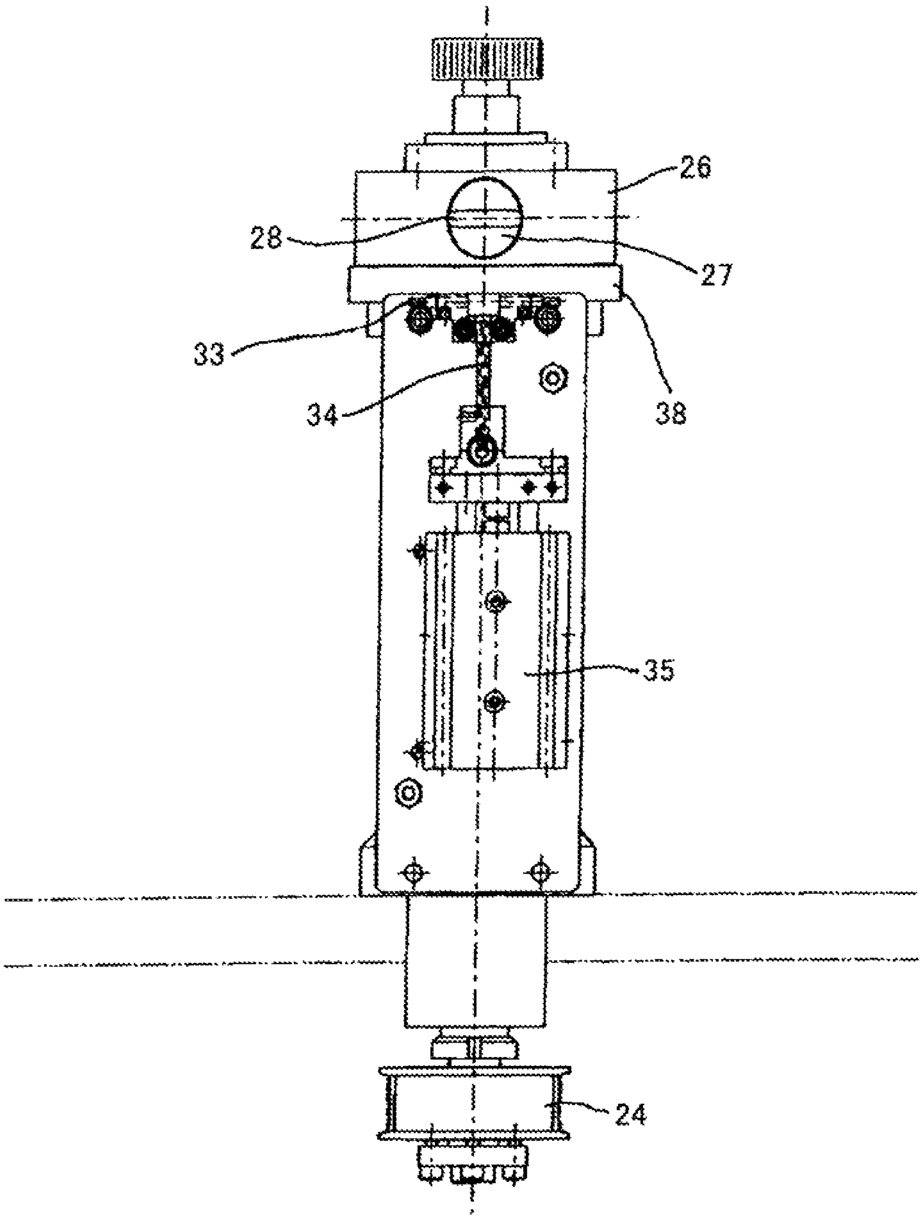
FIG. 9 is a front view of a turntable having a rotary body, which is a part of FIG. 7.

FIG. 9 is a diagrammatic front view of the turntable 26. The rotary bodies 27 are rotatably supported via the shaft at four positions on the outer periphery of the turntable 26, and thin engaging strips 28 project from the respective rotary bodies 27. Then, the base 38 is provided on the lower side of the turntable 26, so that the container body 2 of the container 1 fitted into the hole 32 and projecting downward of the base can be detected by a sensor 33 provided downward of the base

38. Then, a push-up pin 34 is attached below the hole 32, and the push-up pin 34 can move vertically by the action of the air cylinder 35.

In order that the turntable 26 rotates, in the case of the container 1 in the state shown in FIG. 8A, it is necessary to push up the container body 2 of the container 1 fitted into the hole 32 and, in the case of the container 1 in the state shown in FIG. 8B, it is necessary to slightly push upward the cover member 3 which is fitted partly at a lower end. In any case, however, the container 1 can be pushed upward by causing the push-up pin 34 to be moved upward by the action of the above-described air cylinder 35. The rotary body 27, having received the container 1 by the rotation of the turntable 26 in a state of being pushed up to a predetermined height, moves to rotate by 90° at this position.

When the turntable 26 moves to rotate by 90°, the engaging strip 28 projecting outward of the rotary body 27 as shown in FIG. 7 is fitted to a depressed groove of an engaging portion 36 and engage the same. Since the engaging strip 28 forms an elongated horizontal portion, it is fitted to a depressed groove, which is notched also horizontally by the rotation of the turntable 26. Therefore, when the engaging portion 36 rotates by 180°, the engaging strip 28 and the rotary body 27 engaging the depressed groove of the engaging portion 36 also rotate by 180°.

Therefore, the container 1 fitted in the inverted orientation in the receiving hole 25 of the rotary body 27 is corrected in its orientation and is inverted so that the container body 2 is positioned on the lower side and the cover member 3 on the upper side.

In the embodiments shown in FIGS. 2A to 2C and FIG. 6, the orientation of the container 1 is detected by the sensor 33 and, when the container 1 is in the correct orientation, the above-described engaging portion 36 is not rotated, while when the container 1 is inversely oriented, the engaging portion 36 can rotate by 180° to correct the orientation of the container 1.

Incidentally, at a timing when the orientation of the container 1 is corrected, the cover member 3 is removed according to the steps shown in FIG. 6, and then the liquid medicine 37 or the like is poured into the container body 2 in the present invention. Then, alter having poured the liquid medicine 37 or the like into the container body 2, the container body 2 and the cover member 3 are fitted to each other. According to the method of the present invention, when performing this fitting step, the fitting is performed under an atmosphere at a negative pressure as shown in FIGS. 2A to 2C so that the pressure in the container 1 does not increase to the atmospheric pressure or hither.

At timing when the cover member 3 is attached to the container body 2, the cover member 3 is sealed so as not to be detached. Subsequently, the procedure goes to a drying step in order to dry glue used for the sealing, and the drying step is performed. The sealing method and the drying method are not included in the present invention, and these are not limited. In addition, the method of filling the liquid medicine 37, or the powdered medicine or the granular medicine, and the method of removing the cover member 3 are not limited.

The method of coupling the container body and the cover member according to the present invention is an effective method for the containers formed by fitting the container body having the cylindrical portion and the closed bottom portion and the cover member having the cylindrical portion and the closed top portion, specifically when coupling the container body and the cover member in a capsule or the like for medicine.

The invention claimed is:

1. A method comprising:

providing a container body having a first cylindrical portion and a closed bottom portion;

providing a cover member having a second cylindrical portion and a closed top portion;

filling liquid medicine, powdered medicine, or granular medicine into the container body; and fitting the container body to the cover member to form a filled container;

wherein, in said fitting of the container body to the cover member, the container body is fitted to the cover member in an environment at a pressure lower than atmospheric pressure;

wherein said fitting of the container body to the cover member is performed using a jig including a container body receiver arranged on a lower side and a cover member receiver arranged on an upper side, wherein the container body receiver includes a first inner wall defining a receiving portion for receiving the container body, an inner wall bottom formed at a bottom portion of the first inner wall for placing the closed bottom portion of the container body, and a through hole formed on the inner wall bottom so as to be arranged coaxially with the receiving portion, wherein the cover member receiver includes a second inner wall defining a hole portion having substantially the same diameter as the receiving portion and a shoulder portion formed on an upper portion of the cover member receiver for retaining an open lower end portion of the cover member, wherein the shoulder portion is formed into an annular shape arranged coaxially with the second inner wall, and the container body receiver and the cover member receiver are disposed so that the receiving portion and the hole portion are arranged coaxially with each other, the second inner wall and the first inner wall including the inner wall bottom and a side wall of the through hole are formed respectively with a first groove, a second groove and a third groove communicating with each other, a pipe is disposed on the lower side of the container body receiver so as to communicate with the third groove, and a push-up pin movable in the vertical direction is disposed in the pipe so as to be arranged coaxially with the through hole, and in said fitting of the container body to the cover member, the container body is received by the receiving portion, the cover member is placed on the cover member receiver so that the open lower end portion is retained by the shoulder portion, the cover member receiver is placed on top of the container body receiver so that part of the container body is inserted into the hole portion, the push-up pin is driven upward via the through hole to push the container body up with the push-up pin and fit the same with the cover member in a state in which gas in the receiving portion and the hole portion is sucked via the pipe and the third groove, the second groove and the first groove.

* * * * *